United States Patent [19]
Estabrook et al.

[11] Patent Number: 5,911,706
[45] Date of Patent: *Jun. 15, 1999

[54] DEVICE FOR SUBCUTANEOUS ACCESSIBILITY

[76] Inventors: Brian K. Estabrook; Frank Prosl; Dale Whipple; Robert D. Gage, all of c/o Biolink Corporation 47 East Grove St., Middleboro, Mass. 02346

[*] Notice: This patent is subject to a terminal disclaimer.

[21] Appl. No.: 08/758,337

[22] Filed: Dec. 3, 1996

[51] Int. Cl.⁶ ........................................ A61M 5/00
[52] U.S. Cl. .......................... 604/116; 604/93; 604/167
[58] Field of Search ................... 604/264, 280, 604/93, 116, 164, 165, 167, 169

[56] References Cited

U.S. PATENT DOCUMENTS

| | | | |
|---|---|---|---|
| 5,226,879 | 7/1993 | Ensminger et al. | 604/93 |
| 5,290,243 | 3/1994 | Chodorow et al. | 604/165 |
| 5,437,643 | 8/1995 | Transue | 604/164 |
| 5,520,643 | 5/1996 | Ensminger et al. | 604/93 |
| 5,527,277 | 6/1996 | Ensminger et al. | 604/93 |
| 5,533,974 | 7/1996 | Gaba | 604/110 |

*Primary Examiner*—Wynn Wood Coggins
*Assistant Examiner*—Deborah Blyveis
*Attorney, Agent, or Firm*—Edwin H. Paul; Stephen Y. Chow; Jerry Cohen

[57] ABSTRACT

An implantable single or dual-lumen or more lumen device for repeated accessing vessels within a body. The device uses a resilient material to form a seal, and has a smooth streamlined flowpath with no flow discontinuity. The device is joined to a catheter, in most cases, such that fluids can be extracted from or injected into the vessel to be accessed. The device is designed for the high flowrates, on the order of 150 and greater milliliters per minute, associated with hemodialysis, plasmapheresis, and other fluid exchange therapies. In such applications smooth flow streaming is important to minimize damage to the blood. A corresponding straight-needle apparatus is designed to mate and lock with the access device, where alignment and open flowpath is ensured. A valve seal incorporates opposing very hard surfaced guide elements that are retained and in intimate contact with the seal itself. The needle assembly pushes open these guide elements which open the seal before the needle point reaches the seal material.

24 Claims, 8 Drawing Sheets

DEVICE FOR SUBCUTANEOUS ACCESSIBILITY

CROSS REFERENCE TO RELATED PATENTS

Priority is claimed under 35 U.S.C. § 120 on the U.S. application Ser. No. 08/485,498 filed on Jun. 7, 1995 entitled, HEMODIALYSIS ACCESS APPARATUS, and to U.S. application Ser. No. 08/661,903 filed on Jun. 12, 1996 entitled, IMPROVED DEVICE FOR SUBCUTANEOUS ACCESSIBILITY. Both of these applications are of common assignment with the present application

FIELD OF THE INVENTION

The present invention relates generally to apparatus that allows access to the vascular system of a human (or other animal), particularly for the high-volume fluid flow required in hemodialysis, plasmapheresis, and other fluid exchange therapies. More particularly, the present invention relates to a septum-less subcutaneously implantable access of single or dual-lumen construct and a mating needle apparatus.

BACKGROUND OF THE INVENTION

There exists a class of devices for accessing fluid spaces and vessels within a human (or animal) body that are generally referred to as "ports". Herein, "vessel" is defined as any conduit carrying a fluid within the patient's body. These prior art devices comprise a chamber having an access opening sealed by means of a septum and having an egress from a second location leading to a catheter disposed within a fluid space or vessel. The septum allows a needle to pass into the chamber, but then closes when the needle is removed, thereby preventing fluid leakage from within a space or vessel and also anything from entering or exiting the chamber. These devices are usually implantable below the skin to prevent infection, other contamination, and mishandling.

Ports are designed for relatively infrequent use, perhaps once a week, and, importantly, for flow rates of 50 milliliters per minute or less, as is common during chemotherapeutic treatment. Modification of these devices for hemodialysis, plasmapheresis, and other fluid exchange therapies, which require much greater flow rates, by simply enlarging the device components, poses several serious drawbacks that effectively limit use in such applications. First, the septum degrades quickly due to the larger gauge needles necessary to accommodate the flow rates required in hemodialysis. Repeated puncturing of the septum by these large needles produces numerous free-floating septum fragments that can find their way into the circulatory system. Accordingly, the useful life of the devices is substantially shortened, thereby defeating one of the purposes of using an implantable subcutaneous device. Second, the flow path has several stagnation points where clots may form and also is not completely flushable or easily cleaned, thereby providing breeding grounds for infection, once contaminated or a build-up of material which may adversely affect function. Third, the flow path is not streamlined and contains flow path obstructions, sharp corners, and abrupt changes in flow area and flow direction. This tends to increase the shear stress and turbulences experienced by blood flowing through the device due to the significantly higher flow rates required in hemodialysis, thereby increasing erythrocyte damage and platelet activation. Also, the tortuous flow path increases the flow path resistance and the pressure drop through the devices, such effects can increase air release and foaming, causing the dialysis machine's safety alarms to activate.

A general limitation in all relevant prior art devices is the lack of a streamlined flow path. Without such streamlining, stagnant volumes exist where clots may form and shear stress is higher, tending towards erythrocytic damage. Such locations cannot be flushed or easily cleaned. Blood residue remaining in the devices after flushing may clot and provide breeding grounds for infection, once contaminated. In addition, pressure drops and abrupt flow direction changes may damage blood components.

The present invention is also useful for other liquid or fluid (including gases) transfer purposes into and out of human and animal bodies, including the transfer of externally prepared solutions for cleaning, flushing, dialysis, chemical agent delivery, transfusions, blood donation, insufflation, wound drainage, etc.

Accordingly, it is a principal object of this invention to overcome the above illustrated inadequacies and problems of extant devices by providing a totally implantable access means suitable for repeated use in applications (e.g., hemodialysis with blood flow rates of 250 milliliters per minute or more yet with low pressure drops along the flow path).

It is another principal object of the invention to optimize fluid flow in hemodialysis particularly and in other applications referred to generally, above.

It is another object of this invention to provide a substantially laminar flowstream It is yet another object of this invention to minimize flow discontinuities and to substantially match the internal diameters of the injecting cannula and the receiving catheter, and a related object is to bring the exit end of the cannula and the entrance end of the catheter into close proximity.

It is a further object to provide means where the flow path is streamlined and provides substantially no stagnation points, no flow discontinuities, and also to provide an apparatus where the entire flowstream is flushable.

It is a further object to the invention to minimize internal fluid collection zones or stagnant volumes in such a device.

It is a still further object to have lower clotting, stenosis, and infection rates than synthetic grafts.

It is yet another object to have lower infection and lumen clotting than percutaneous catheters.

It is a still further object of this invention to provide apparatus suitable for single and dual-lumen catheter systems.

It is yet another object of this invention to provide an access device that is less painful during needle insertion and more accommodating during dialysis for the patient.

It is a further object of the invention to minimize irritation and other adverse effects associated with intermittent skin puncture over a course of days, months or years of repetitive access.

It is a further object to secure the needle within the access device during the dialysis session.

It is a further object of the invention to enhance the devices to more effectively lock in a cannula to the device to avoid inadvertent separation, yet allow ease of deliberate release of the cannula.

It is another object of the invention, when using dual-lumen catheters, to secure both needles to each other.

It is a further object of the invention to provide ease of manufacture and assembly of such device consistent with enhanced locking.

A further object of the invention is to establish economy of the lock devices for disposability.

It is a further object of the invention to provide enhanced cannula and obturator handling external to a patient via hub devices coordinated with the structure and functions of the locking devices.

It is also an object of the invention to accommodate multiples of the foregoing objects together.

SUMMARY OF THE INVENTION

The foregoing objects are met by a single subcutaneously implantable device for accessing a vessel within a patient's body, or a ganged pair of such devices or separate such devices, each device including (a) an access guidance means having an entrance and passageway for receiving a cannula and accommodating a locking means for the cannula, (b) flexible locking means, (c) needle guidance means of sufficient hardness to prevent scoring or chipping, (d) valve means for allowing access to a vessel when a cannula is inserted into the device and preventing fluid flow through the device when the cannula is withdrawn, the valve means having a closable passageway that accepts an inserted cannula and comprising an access portion, a sealing portion, and a distal portion; (e) a catheter attachment having a closable passageway with seating means disposed therein, and (f) a shell capable of enclosing these elements.

A resilient elastomeric means for producing a contact sealing pressure is arranged around the sealing portion of the valve means. This resilient means includes, in a preferred embodiment, a cylindrical band made of an elastomeric material that provides forces on the sealing portion and is located outside the fluid path. The sealing portion ordinarily prohibits fluids from passing the seal. But when a mechanical device is inserted percutaneously, and guided to the valve's access portion by the access guidance means, the mechanical device engages the needle guidance means disposed within the access portion of the valve with sufficient axial force to overcome the radial force exerted on the sealing portion by the resilient means for sealing. It is important to note that the needle assembly forces the guidance means and the guidance means pushes the sealing portion open. The needle assembly, actually the obturator in a preferred embodiment, then enters the opened sealing means without the point puncturing or cutting the sealing means. The needle guidance means itself opens the slit to allow the needle assembly to enter and then to slip through the sealing means. So in this fashion the needle assembly passes through the valve until it engages the catheter attachment seating means. This operation provides access through the valve to the valve's distal portion and, ultimately, the vessel lumen, as the distal portion of the catheter that is attached to the access device via the catheter attachment, extends into a vessel lumen. An advantage of the present invention is found by minimizing the spacing between the end of the cannula and the beginning of the catheter, and by smoothly fairing the internal surfaces of the short connecting or transition passageway to the interior surfaces of the cannula and the catheter. If there are disparate internal diameters the short connecting transition passageway smoothly and uniformly accommodates the internal diameters. This arrangement provides a flow path with minimum flow discontinuities and a path that is easily flushed.

The catheter maybe flexibly attached to the surrounding tissue supporting the catheter, but the flexibility allows the device's position to move relative to the surrounding tissue. A strain relief assembly may also be provided at the catheter attaching end of the device to relieve the tension on the catheter attachment to the device to prevent the catheters from kinking. Edges of the strain relief structure can be sutured or stapled to tissues and the strain relief wrap can in turn hold other portions of the device.

The access device may be flexibly anchored to the surrounding tissue. In a preferred embodiment this anchor means is attached to the device to allow the cannula entrance of the device to be rotated, preferably as much as 50 degrees relative to the anchor means in at least two directions. This, together with the normal movement of the skin allows the needle assembly to enter the skin at a location on the skin that is healed, or at least a skin location that has had ample time to heal. This ability to access larger areas of skin for inserting the needle assembly is a significant advantage over relatively fixed ports.

The resilient means for sealing is arranged and constructed to close the valve's potential lumen such that the longitudinal transition profile of the valve's access portion forms a particular shape. The shape of the access portion allows for the generally conical point of the needle obturator to open or push apart the access portion and the slit in the sealing portion with wedging action as the point is pushed through the seal. The axial point pushing force overcomes the radial biasing force exerted by the resilient means for sealing and the internal stresses of the sealing portion as the point enters the sealing portion without cutting the valve material. Because no cutting occurs, no particles of valve material are generated, as is common with septums in ports now in use. Furthermore, the number of penetration cycles to failure in the present invention is significantly higher than with septum ports, as negligible damage occurs during needle penetration.

The flow path transitions between the cannula lumen, the short connecting passage in the access device, and a catheter lumen are arranged and constructed to provide for maximum smoothness and continuous flow paths without abrupt changes in flow diameter and only gentle changes in flow direction. All narrowing and broadening of the flow path is gradual, with angles of preferably 25 degrees or less.

The invention also provides for a hollow needle apparatus or cannula with an outside diameter that matingly corresponds to the entry passageway of the access device, and an obturator that is inserted into the needle lumen filling the lumen and which has a tip portion that extends beyond the cannula. This needle/obturator combination provides a needle assembly with a pointed end, and an outer surface having smooth transitions, which are formed to puncture tissue easily and to open the valve without damaging it. The hollow needle is preferably metal so that the needle wall is as thin as possible considering the stresses on the needle. This is important since the larger the internal diameter of the needle the lower is the flow resistance. The lowest flow resistance consistent with the physical constraints and needs of the patient and the function being performed, especially in the high flow rate hemodialysis field, is an important goal of the present invention and a major advantage of the present invention.

The flexible lock preferably comprises a resilient plug (preferably made of a medical quality elastomer) surrounding an inserted hollow metal cannula, but containing rigid internal blades or strips (preferably made of super hard material such as a hard ceramic or hardened metal, e.g. titanium nitride) that extend radially in locking use and are configured and arranged to inscribe the outer cannula surface and bear on it with a high reaction force. When an inadvertent axial pull on the needle from outside (or the push of a muscular contraction from within) places an expelling force on the needle, the beginning of movement increases the locking effect. The blades or strips have inner edges that form one or more teeth of pointed or blunt ends, such teeth having shallow clearance angles with respect to the passage axis. The blades have outer edges that are locked in geometrically by a tapered inner surface of the shell.

Deliberate removal can be done by rotating and/or wiggling (spiral or combination of axial/rotation movements) of the cannula so that the orientation of the blades shifts from essentially radial to essentially chordal or non-radial alignment relative to the device's internal passage axis. When the plug and blades are disposed non-radially the cannula can be withdrawn easily. The rotation or the like is then relaxed (after complete removal of the cannula) and the blades are restored to radial alignment by the elasticity of the plug. When the needle is reinserted (typically one or more days later) the entering cannula passes through the inner edges of the blades.

Generally there is a full withdrawal of a cannula or a full insertion; but partial insertion and/or withdrawals can also be accommodated. The resilient plug body is set radially apart from the cannula surface to avoid shedding or uneven friction due to thermal conditions or other sources of expansion/contraction of the flexible plug (e.g., made of silicone rubber). The flexible plug material is preferably cast in a mold about the aligned (radial) blades. Holes or the equivalent are provided in the blades so that the flexible material on both sides of each blade is bridged via such holes or other means and the blades are securely aligned therein radially and with inner and outer edges of the blades extending beyond inner and outer plug surfaces. Generally, there is a low axial direction friction meeting of the blade outer edges and the tapered (frusto-conical) shell inner surface. A ceramic shell with a smooth finish inner tapered surface meets this criterion very well. Similarly the blade inner edges slide along the cannula outer surfaces with low friction. The hardness of all such surfaces and the rigidity and dimensional stability of blades, cannula and shell are related to the above features and also important per se.

The valve, in a preferred embodiment, may include a plug of sealing material with a slit cut in the center and with a spring loading means holding the slit closed to block the internal passage of the device when the cannula is withdrawn and yet is readily opened as the needle assembly (obturator) is inserted without damage as described above. Similar valves can be used with more than one slit opening and closing as described above. In any such design, it is preferable to have automatic spring loaded closing when the cannula is withdrawn and easy opening as a needle assembly or the like is inserted through the device's internal passage to maintain contact sealing stress when closed. The present invention causers no cutting due to the manner of opening the seal described above.

Ease of use and product reliability are also accommodated by features discussed below.

The invention also includes an extracorporeal needle assembly hub structure or pair of such structures usable in combination with the implantable subcutaneous access device(s) for straight cannula alignment and aligned cutter and stiffener (a separate element or integrated with the cannula) that has to penetrate the skin, find the entrance to the inner passage of the subcutaneous device and pass through it to a lock-in site therein without coring the skin. The hub has a Y-connection of three internal paths: (a) external fluid passage, (b) passage to the cannula and (c) a cannula/cutter access leg, all cooperating with shallow bend angles and gradual curvatures at the Y-intersection in the fluid path and straight line access to the needle assembly locking device, as consistent with practical and economic mass production while achieving a benign flow path which does not damage cellular blood components and meets previously stated criteria for the blood path.

The needle is initially inserted through the hub structure (or comes preassembled with it) and has an internal obturator with a point that passes out of the needle distal end for penetrating skin and subcutaneous tissue and serving as an aid to finding the subcutaneous entrance to the access and lock device. The obturator point is faceted so that its cutting is done along meeting line edges of the facets. However, when the obturator point has cutting edges that extend from the center towards the outer surface of the obturator. but as cutting edges extend to the outer surface of the obturator the edges are softened or dulled so that the obturator does not cut, score, or otherwise mar the internal wall of the passage or interiors of the locking and sealing components of the access device which form part of the passage. The obturator edges are softened in a preferred embodiment by facets but in a larger number of facets, set at shallower angles, than the facets at the point. In yet another preferred embodiment the facets are concave rather than flat, where the intersection of the facets provides a sharper edge. The section of the obturator with the dulled edges blends into a beveled end of the cannula. Once the needle assembly is fully inserted, locked and sealed in place, the obturator can be withdrawn to leave a smooth flow path beginning in the needle hub structure and continuing therein to a smooth blending with the proximal cannula region of the hub structure and continuing through the full length of the cannula to emerge at the distal end and in turn blend smoothly with the device's internal transition passage and then into the implantable catheter within the patient.

The presently claimed access device is suitable for both single-needle and standard hemodialysis, plasmapheresis, and fluid exchange therapy applications. For standard applications, which require two flow paths, the housing may be arranged and constructed to engage two needle hub assemblies, as described above, and include dual-lumen through passageways. When two needles and needle hubs are used, a bar may be provided that engages each needle hub, thereby locking both needles to each other to preclude inadvertent disconnection of only one needle, thereby enhancing patient safety. In another preferred embodiment the two needle hubs are prevented from moving laterally with respect to each other.

It is important to note that the primary object of this invention is to provide an implantable, subcutaneous access device suitable for applications requiring flow rates of 250 ml/min or greater, with low pressure drops along a streamlined flow path having substantially no stagnation pints or other flow discontinuities. Low pressure drops and substantial elimination of stagnation points are achieved by having maximum internal diameters of the flow path (and therefore thinnest cannula walls), smooth transition points where different elements of the device abut (e.g., the cannula-transition element-catheter interface) and by having all changes in lumen diameter be of a gradual nature and having straight or nearly straight flow path without sharp curves or objects protruding into the flow path and no dead volume.

As indicated earlier, because such large flow rates are desired with low resistance, it is necessary to have the largest needle outside diameter that patients will accept. Accordingly, rigidity of the puncture needle is desired. A rigid needle allows a greater inner lumen diameter per outer component diameter (i.e., thinner walls) than does a flexible tube. This is important because it allows the needle to have as small a cross-sectional diameter as possible, thereby lessening the trauma on the patient's puncture site, yet still be capable of handling large flow rates. Flexible tubes require a much higher outer diameter to inner diameter aspect ratios to prevent kinking or tube collapse. Thus, to accommodate the bloodflows common during hemodialysis, a much larger outer diameter would be required if flexible materials were used. Also, a rigid needle allows a greater force to be transmitted to open the seal valve by overcoming the resistance provided by the spring. Thus, a greater contact sealing force can be employed, resulting in a more robust, reliable, and fault-tolerant valve seal.

Further, the lack of sharp angles or bends in the flow path is much less injurious to fragile hematocytes. Since the flow path from needle to catheter (or vice versa) is substantially straight, the fluid turbulence is minimized, the shear stresses are lessened, and flow directional changes are minimized resulting in less erythrocyte damage and a lowered tendency toward platelet activation.

Finally, a medically acceptable, water-based lubricant can be used on the needle exterior, as an enhanced lifespan has been observed when lubricant is used. Also, a lubricated needle will penetrate the skin with less pain to the patient.

Other objects, features and advantages will be apparent from the following detailed description of preferred embodiments thereof taken in conjunction with the accompanying drawings in which:

BRIEF DESCRIPTION OF PREFERRED EMBODIMENTS

Referring to the FIGS., wherein like reference numerals represent like parts throughout the several views, it is understood that the device is bilaterally symmetrical through the various cross-sections taken and that corresponding halves of parts shown in cross-section represent cylindrical structures. It is further understood that the present invention contemplates a single implantable access device that accommodates a single needle/catheter fluid passage or a ganged plurality of such passages, or separate such devices, each accommodating either a single or ganged plurality of such passages.

Turning now to the drawings, FIGS. 1–8 show a dual-line channel embodiment of the implantable access device with corresponding cannula/obturator assemblies of the present invention. Access device 10, implantable just under the skin S of a patient, comprises a needle guidance element 12, a catheter locking element 16, and a protective cowling 14 accommodating these and related internal elements. For purposes of this discussion, it is understood that the embodiment contemplates dual passages; however, solely for simplicity of description, the elements will be referred to in the singular, as though only one passage were present.

Anatomical Mounting Plate

Referring back to FIG. 1A–1E, the mounting plate 60 has a plurality of eyelets 98 for suturing attachment to subcutaneous tissues. As discussed previously, the anatomical mounting plate attached to device 10 by means that allow the plate to pivot in relation to the device. This allows, in sequential hemodialysis sessions a day or two apart, the device 10, with ganged access to internal catheters to be pivoted to allow needle access at different skin puncture sites while other such sites heal.

Protective cowling 14 has a lower surface 58 accommodating an anatomical mounting plate 60 by means of rivet 62 being disposed through lumen 64 of anatomical mounting plate and further through a mating opening in the lower surface of the protective cowling 14.

The arrangement of mounting of the cowling 14 to the plate 60 allows the plate to pivot relative to the cowling 14. There is a shoulder 66 that acts to retain the pivot action by the plate striking the shoulder 66 to a zone of about 30° (i.e., about 15° clockwise rotation and 15° counterclockwise rotation). Other ranges of pivoting can be used and other pivoting mounting arrangements suitable for use herein are known in the art.

There is a protective structure 16 surrounding the ends of a catheter. This structure 16 is attached to the cowling 14 and provides a means to retain the catheters to the device. The catheters may be attached to surrounding tissue to generally retain the catheters and, not shown, a shroud or other such strain relief elements may surround the catheters proximate the device, as is known in the art, to protect the ends of the catheters from undue stress or strain.

Figure 1A:
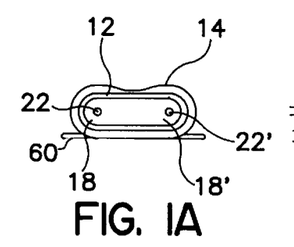
FIG. 1A is a front axial view of an implantable access device of the present invention.
Figure 1B:
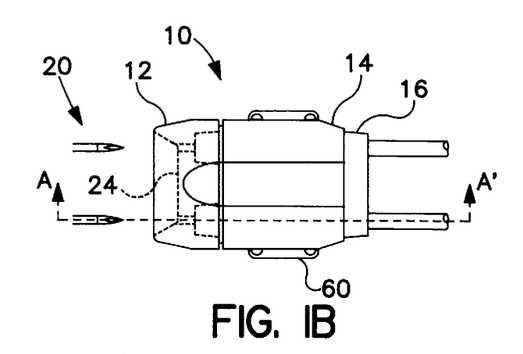
FIG. 1B is a superior plan view of an implantable access device of the present invention.
Figure 1C:
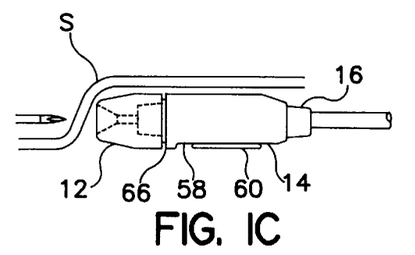
FIG. 1C is a side elevation of an implantable access device of the present invention.
Figure 1D:
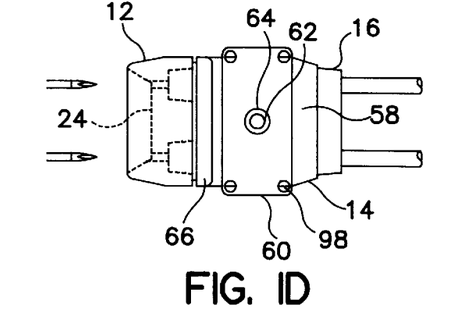
FIG. 1D is a inferior plan view of an implantable access device of the present invention.
Figure 1E:
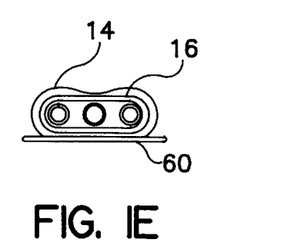
FIG. 1E is a rear axial view of an implantable access device of the present invention.

Focusing our attention on the individual components of device 10, FIGS. 1A–1E show an embodiment of needle guidance entrance 12 of the presently claimed invention. This entrance 12 has a inwardly sloped and concave first end bounded by conical ends 18 and 18' such that a rigid implement, such as needle/obturator assembly 20, is guided to either entrance lumen 22 or lateral trough 24. The trough has a rounded cross section as shown in FIG. 1C, and the lowest surface of the trough is a straight connection between the two entrance apertures 18 and 18'. If the implement contacts trough 24, there is no structure or slope to impede the lateral movement of the implement to either aperture.

Figure 2A:
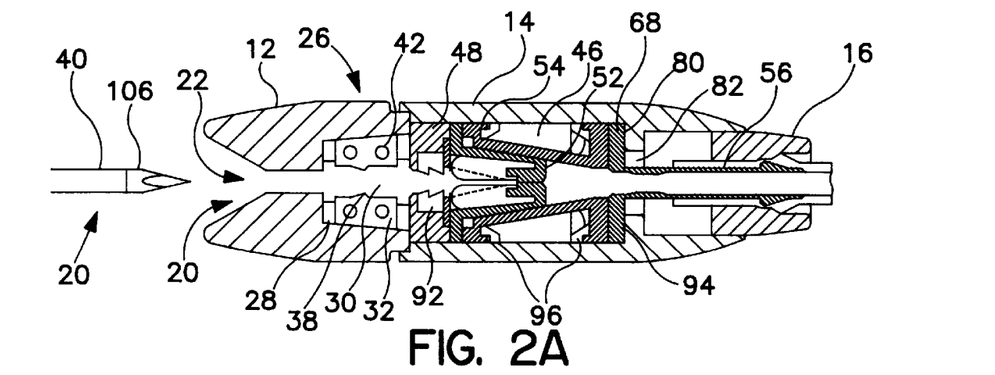
FIG. 2A is a cross-sectional view of the implantable access device of FIG. 1B taken through the line A–A' with a corresponding cannula/obturator assembly not inserted.
Figure 2B:
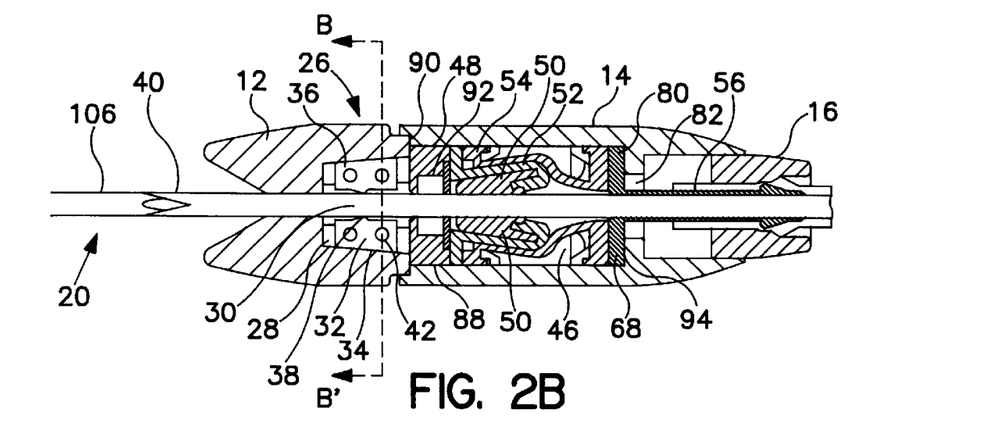
FIG. 2B shows the device of FIG. 2A with the corresponding cannula/obturator assembly inserted.

FIGS. 2A and 2B show an embodiment of lock assembly 26 in each channel of the dual lumen device. Lock assembly 26 comprises a silicone rubber plug 28 with a hollow elongated passage 30 therein accommodating the inserted needle with some clearance and one or more (preferably three, but variable from one to ten) radial locking blades 32. The blades 32 can be rectangular in longitudinal cross section or tapered as shown.

Figure 3A:
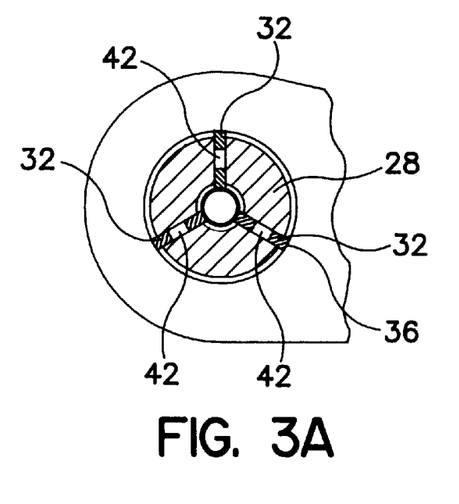
FIG. 3A is a cross-sectional view through the line B–B' of FIG. 2B.
Figure 3B:
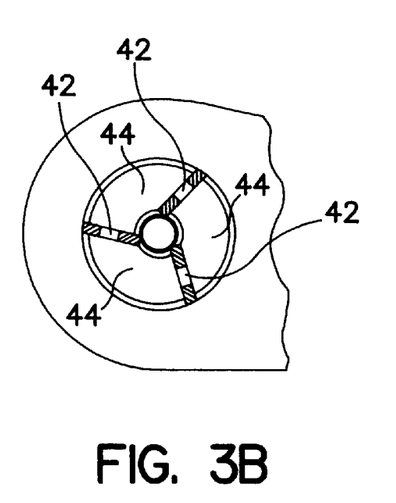
FIG. 3B is the same view of FIG. 3A with the cannula twisted.

Referring to FIGS. 2B, 3A and 3B each blade 32 has an axial-direction-tapered outer edge 34 tapering towards the guidance element 12 entrance 22 and the guidance element 12 has a corresponding taper 36. FIG. 3A and 3B are cross sections through B–B'. Each blade also has an inner edge 38 which comprises one or more teeth preferably of shallow clearance angle ending in a point or small length contact with the cannula outer surface 40. Each blade has holes 42 allowing the plug to be continuous and retain the metal blades in relative positions to the rubber body and to each other. FIG. 3A shows the locking blades 32 hard against the cannula outer surface locking the cannula to the device. FIG. 3B which is a cross section as in FIG. 3A except showing the effect of twisting the cannula so that the blades are not aligned radially to the cannula. The locking blades 32 pivot about their outer edges and the inner edges 38 and teeth move away 44 from the cannula and provide little retaining force on the cannula. Twisting the cannula while axially withdrawing the cannula allows the cannula to be extracted with little force. To accommodate this withdrawing, the cross section of the blades may be tapered from the outer edges 34 to the inner edges 38. After the cannula is withdrawn, the plug and blades return to the original position, shown in FIG. 3A.

Figure 3C:
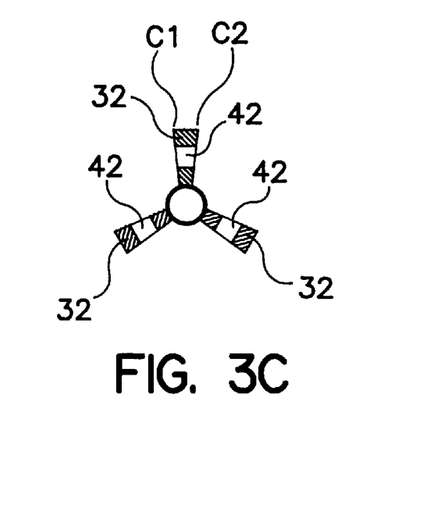
FIG. 3C is an alternate pictorial of the locking blades (distorted for illustration)
Figure 3D:
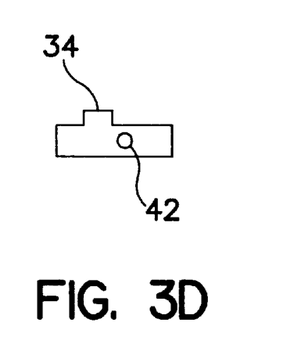
FIG. 3D is alternative blade design.

Other forms of the blades are shown in FIGS. 3C and 3D. In FIG. 3C, the blades 32 are cross-section tapered (distorted for illustration) to establish corners C1, C2 as pivot points for accommodating tilting of blades from radial to non-radial alignment as cannula 40 is twisted. FIG. 3D shows a form of blade that has a limited length outer edge 34 compared to blade length as a whole. The blade can be rectangular in cross-section or tapered as in FIG. 3C. It is contained in the plug without a need for holes, but one such hole 42 can be provided optionally FIGS. 1A–1E, 2A and 2B show an embodiment of a protective cowling 14 that defines a space 46 capable of accommodating needle guidance means 48, needle alignment means 50, a cannula seal 92, flexible valve seal 52, elastomer 54, and transition channel 56. the needle assembly penetrates the locking mechanism 26 and continues through the ring seal 92. This ring seal 92 prevents leakage as the cannula is removed after use. The needle assembly continues to penetrate to the rigid guide elements 50 which force open the slit in the seal 52, as described later. An elastomer 54 surrounds the seal 52, both 52 and 54 are made of elastomeric materials. However, the valve seal 52 is more supple with a lower durometer rating than that of elastomer 54. The more supple material accommodates particles or other small debris that may be attached to the needle assembly and still provides a good seal.

Figure 4A:
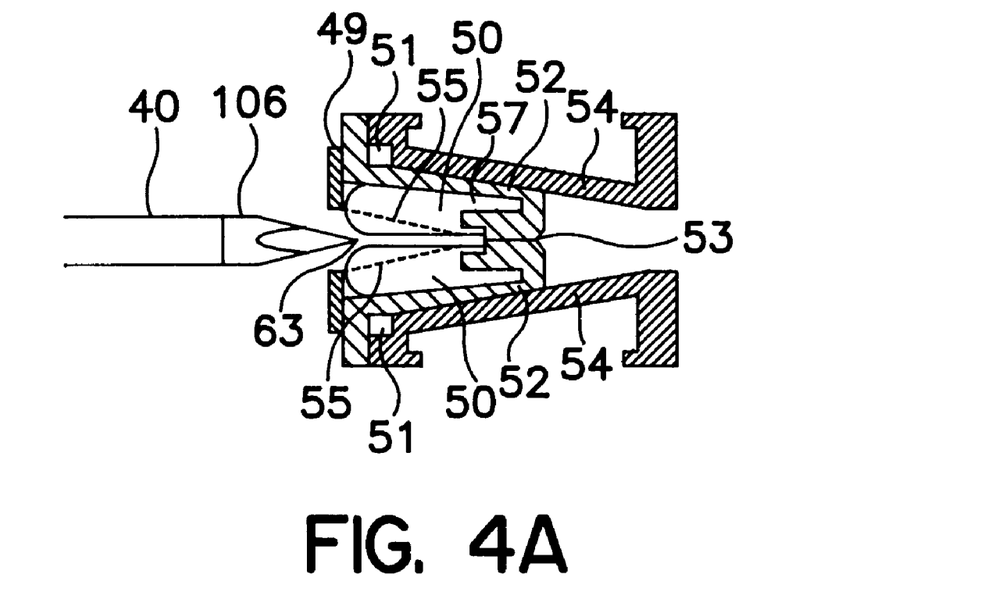
FIG. 4A is a cross sectional view of the valve guides and resilient seal with the needle cannula not inserted.
Figure 4B:
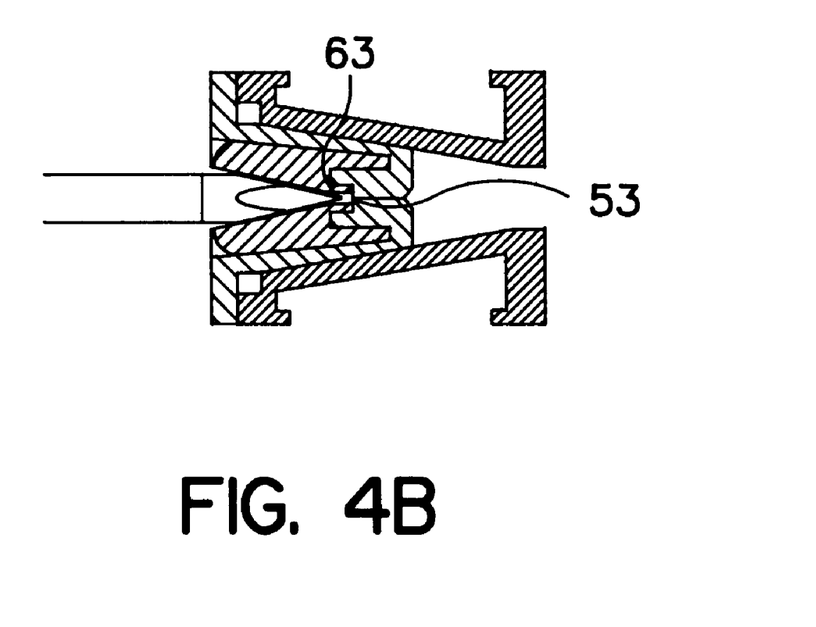
FIG. 4B is the same view of FIG. 4A with the needle cannula inserted.

FIG. 4A shows the obturator tip just before entering the rigid guides 50. The guides are retained by a retaining disk 49 and the seal 52. The device also comprises the above mentioned valve structure, seated between a retaining disk 49, in turn, as shown in FIG. 2A, held at an annular shoulder 90 of needle guidance element 12 and supporting needle alignment ring 92, and catheter connector retaining ring 68, held at annular shoulder 94 of protective cowling 14 (or radial inserts instead of a ring). The valve is maintained in an elongated position, such that it does not dislodge during needle insertion or withdrawal, by retaining element 96 and the cowling. Referring back to FIG. 4A, the valve has opposing guide elements 50 with a surface hardened to a point higher that of the steel used in the obturator. These elements may be made of ceramic or coated with a hard material, like titanium nitride. The valve seal 52 is formed with sealing portion with a slit 53 that is axially aligned with the obturator. The guide elements have extensions 57 that seat in apertures in the sealing portion. This intimate contact of the guide elements and the seal compels the slit to follow the ends 57 of guide elements. When these ends 57 open the slit 53 opens as shown in FIG. 4B. There is a retaining ring 51 encircling the guide elements distal from the slit. This ring 51 acts as a pivot point when the guide elements open. The hardened surfaces of the guide elements are tapered 55 toward the slit and guide the needle assembly to the slit. Referring to FIG. 4B, the outer diameter of the needle assembly or the obturator contacts the guide assembly and opens the guide elements before the point 63 of the needle assembly reaches the slit. As illustrated, the guide elements pivot about the retaining ring. The elastomer material 54 substantially surrounds the seal 52. As mentioned above, the elastomer 54 and the seal 52 are constructed with a differnet durometer levels that separate the sealing attrribute fromt the forcing means. As the guides open, both the elastomer 52 and seal 54 resist the opening and, as the needle assembly penetrates completely through the slit 53, the elastomer and the seal conform around the needle assembly surface to form a seal thereto. The elastomers are providing an inward radial force urging the slit closed. The obturator may be removed and the elastomer 54 is forcing the seal 52 to conform to the outer cylindrical surface of the cannula to form a seal thereto. When the cannula is removed the slit closes by the elastomeric action of the 54 and 52 materials.

Figure 5A:
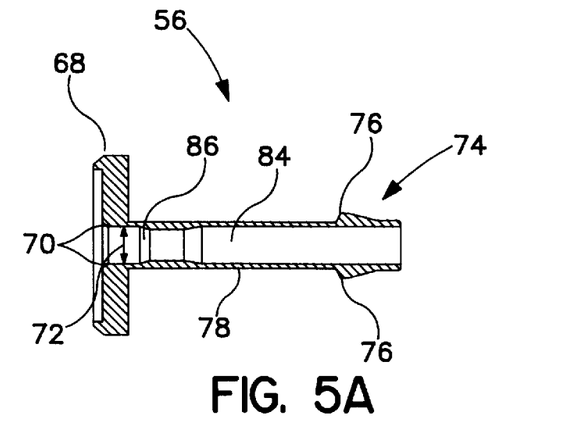
FIG. 5A is a cross section view of the transition channel of an implantable access device of the present invention.

FIG. 5 shows an embodiment of one of the matching pair of connecting transition channels 56 shown in FIG. 2A and 2B. These elements provide a flanged end 68 that is retained in the cowling. The fully inserted cannula matches and mates with the channeled surface 70. The internal diameter 72 matches that of the cannula and the transition channel provides fairing for a transition from the cannula internal diameter to the internal diameter of the catheter. This construction minimizes any flow discontinuities. The 74 end of the transition element has flared extensions 76 and 76'. The catheter slips over these extensions and is retained thereby and by the element 16 (FIG. 2A). FIG. 5 needle/cannula seat/catheter attachment transition channel 56 has a barrel segment 78

Referring back to FIG. 2A, The retaining flange 68 is disposed within space 46 of protective cowling 14, such that it is held at annular shoulder 80 of protective cowling 14, and further, such that barrel segment 78 is disposed within lumen 82 of protective cowling 14. Catheter connector retaining flange 68 itself defines an annular shoulder capable of accommodating valve seating means 54. The transition channel 56 further defines an axial lumen 84 having disposed at some point along its length needle stop 86, shown here as a conical narrowing of lumen 84, although other designs are contemplated. It is imperative to the purposes of this invention, however, that all transitions in lumen diameter be sufficiently gradual as to inhibit damaging delicate blood cells.

Flow in the Access Device(s)

Focusing again on FIGS. 2A and 2B, it is seen that the internal passage can be very short, that a generally straight flow path is established and that the inner diameter of the cannula can be larger than is conventional. These factors reduce the flow resistance and allow the device to accommodate high fluid flow rates with low shear (i.e., lower than state of the art shear rates, generally, and short residence time at highest shear rate zones) and to limit other deleterious effects as to the fluid passing through. The needle assembly (discussed in more detail in connection with FIGS. 6A, 6B, 7A, and 7B below) has an interior obturator nail and surrounding needle cannula sheath that can be of very thin wall construction. Thus for a standard cannula outer diameter of 0.072 in. an inner diameter of 0.0673 in. (compared to a standard of 0.064 in.) can be provided because of obturator reinforcement. That 0.0033 in. difference in inner diameter affords, approximately, a greater than 20% decrease in flow resistance. The obturator also prevents a coring or cookie cutter effect that can arise from using a hollow needle for subcutaneous accessing.

Needle/Obturator Assembly

Figure 6A:
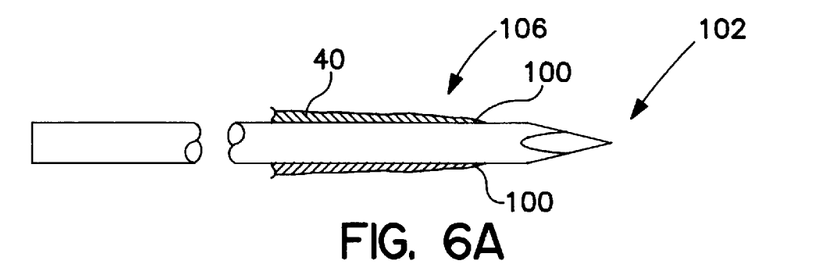
FIG. 6A is a side elevation of the obturator of the present invention.
Figure 6B:
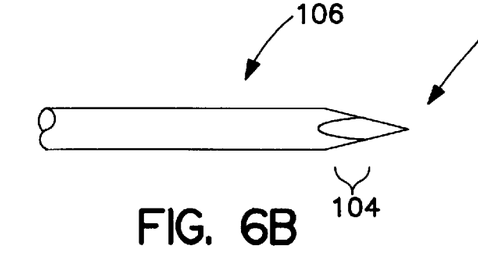
FIG. 6B is a side elevation of the obturator of FIG. 6A rotated 90 degrees.
Figure 6C:
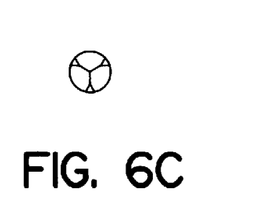

FIGS. 6A, 6B, and 6C shows an axial section of the piercing end of the needle assembly with the needle cannula 40 having a wall end 100 that is beveled to blend with the obturator to lessen the resistance to penetrating tissue and the inventive device. The cannula end 100 also seats firmly on a corresponding conical stop 86 within axial lumen 84 portion of transition channel 56 (FIG. 5). Obturator tip 102 has a distal end with multiple facets (preferably three) as shown in FIGS. 6A and 6B. These facets may be concave to provide sharper cutting edges. The part of the point 104 that blend the cutting edges with the outer surface of the obturator is dulled by providing a greater number of facets providing a smooth transition from point and cutting edges to cylindrical form.

Obturator cutting for skin penetration is done along meeting lines of distal end facets, rather than solely or primarily at the distal point. This avoids pain to the patient, since the cut is over a short length and does not tear skin over a significant length. However, when the obturator point enters entrance lumen 22 of device 10 and passes therethrough, it does not cut, score or otherwise mar the internal wall of the lumen or interiors of the locking and sealing components of device 10 that extend from the lumen.

The dulled section 104 does not score the internal passage of the device. Once the needle assembly is fully inserted and its cannula shell is locked in and sealed, obturator 106 can be withdrawn to leave a smooth flow path beginning in passageway 108 of hub structure 110 (FIG. 8C) and continuing therein to a smooth blending with passageway 112 of hub structure and continuing through the full length of the cannula, the length of the transition channel and then into the implantable catheter within the patient.

Figure 7A:
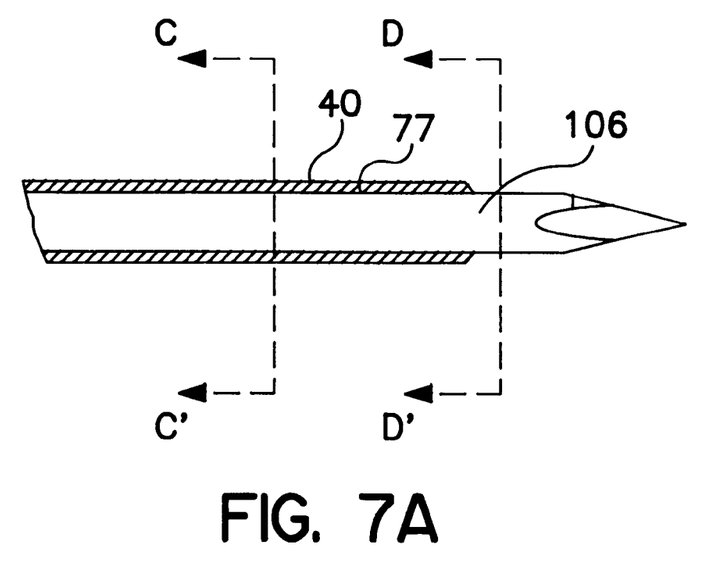
FIG. 7A is a cross sectional view of the cannula/obturator of the present invention.
Figure 7B:
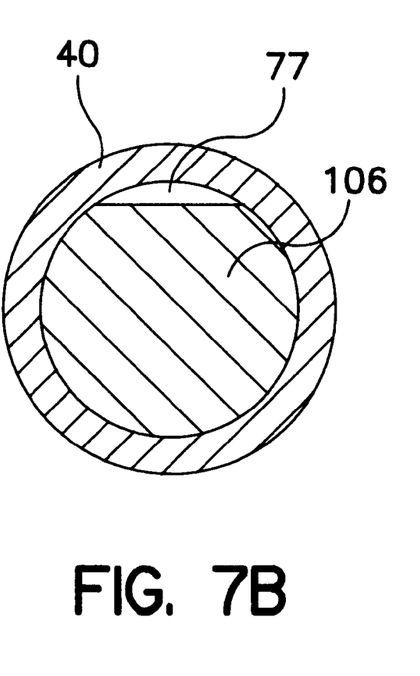
FIG. 7B is a cross sectional view of FIG. 7A taken through line C–C'.
Figure 7C:
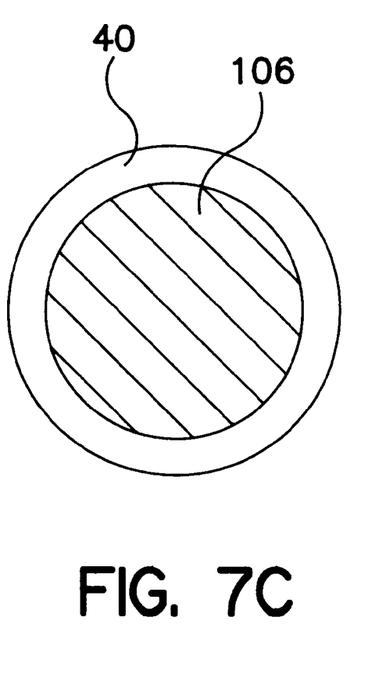
FIG. 7C is a cross sectional view of FIG. 7A taken through the line D–D'.

FIG. 7A shows the needle assembly with a chordal channel 77 cut into the obturator. The cross section of FIG. 7B shows the channel, as compared to FIG. 7C showing the uncut obturator. The passageway allows air to escape while inserting the needle assembly.

Extracorporeal Needle Hub

Figure 8A:
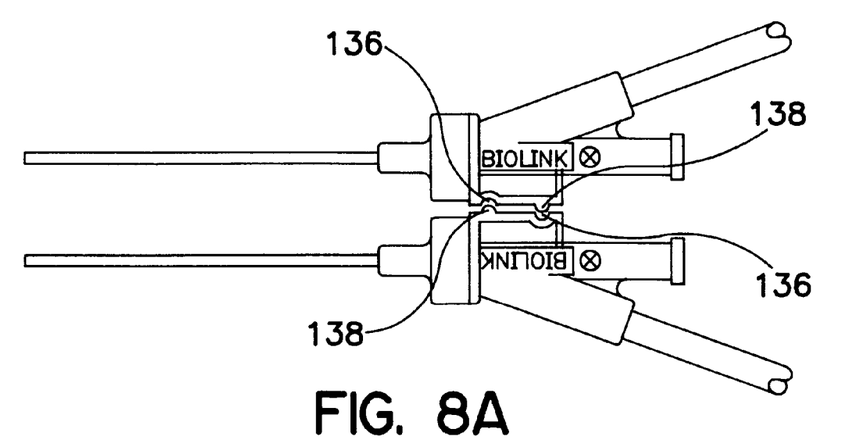
FIG. 8A is a side elevation view of an extracorporeal hub of the present invention being combined.
Figure 8B:
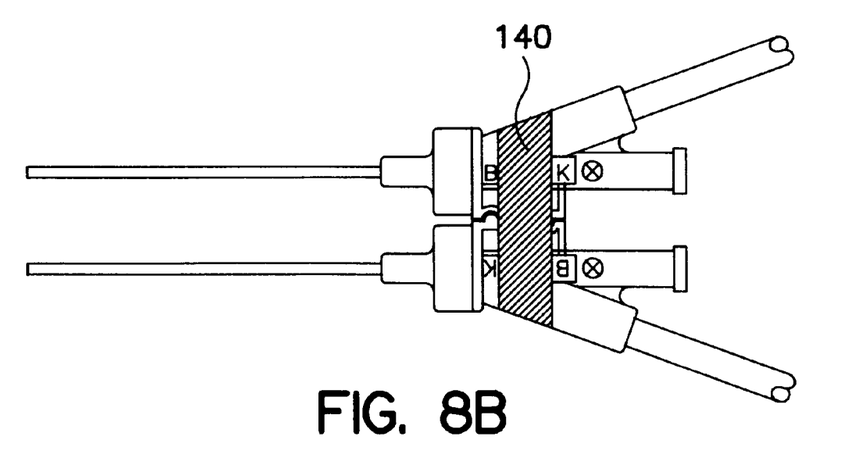
FIG. 8B is a side elevation of the extracorporeal cannula hub attached to one another.
Figure 8C:
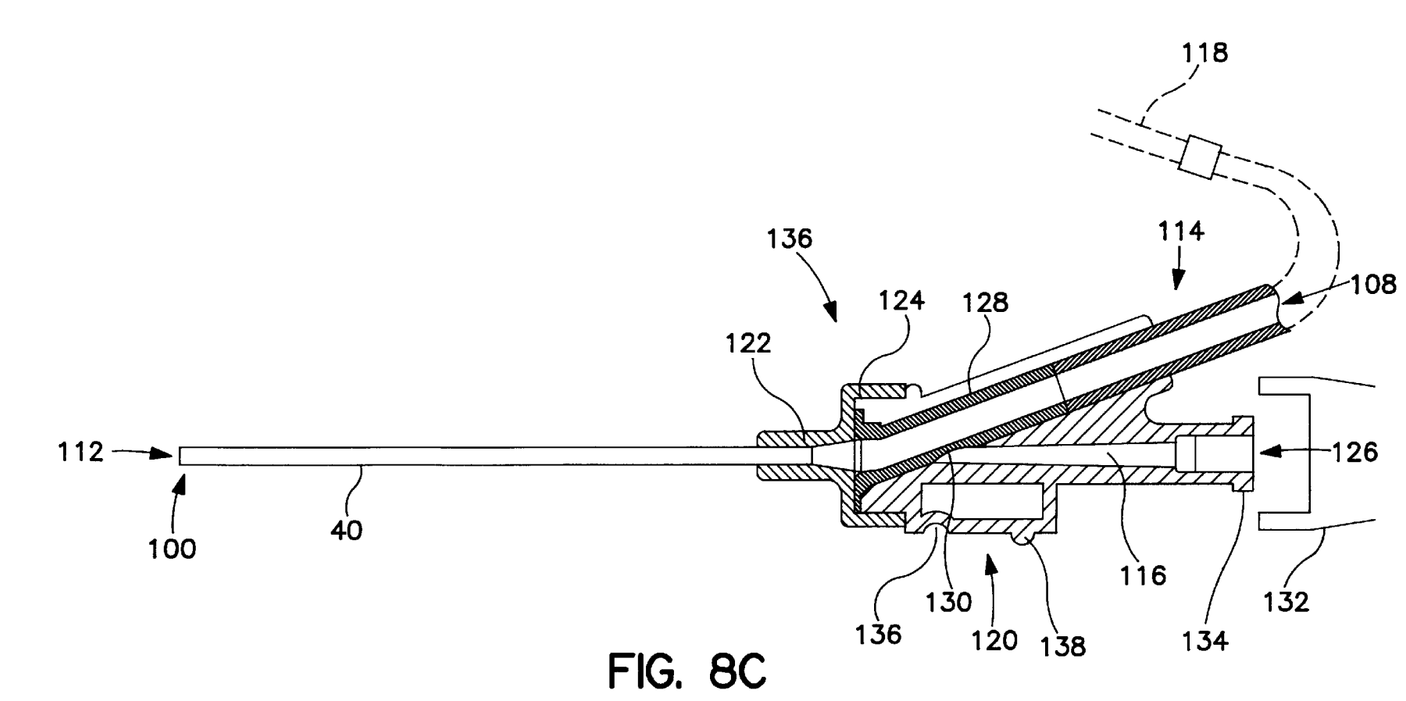
FIG. 8C is a cross sectional view of an extracorporeal cannula hub of the present invention.

FIG. 8C shows an extracorporeal hub structure 110 associated with each access device 10. The hub structure comprises hub body 114 defining a Y-shaped arrangement of three internal passageways 108, 116, and 112 provided, respectively, for connection to a blood line 118 from a dialysis machine, accommodation of obturator 106, such that a long extension of the obturator or an extension rod or linkage connected thereto can be accommodated (in either case with an operating handle that allows axial pushing/pulling of obturator, and the needle/obturator assembly 20). It is contemplated that hub structure 110 comprise two mating halves of plastic, as shown, or metal or ceramic meeting at a surface 120 and as assembled by adhesives, solvent bonding, or other means or cast as a single piece.

Needle cannula 40 terminates within collar 122 and is bonded thereto. Collar 122 is in turn securely attached to operating handle 114 such that collar 122 abuts retaining lip 124 of operating handle 114. Thus, rotating the hub structure as a whole rotates the needle cannula 40 for unlocking the cannula within device 10, as described above. Alternatively an inserted sleeve with dial access can provide a similar control. Passageway 116 flares outward at its proximal end to form control entry 126 for insertion of needle/obturator assembly 20.

Flexible insert 128 is disposed within passageway 108 so that it defines a gradual bend in passageway 108 of sufficient arc to align passageway 108 with passageway 112. Insert 128 has a sealed plug portion 130 closing off passageway 116 where it communicates with passageway 108. Sealed plug 130 is pierced by obturator on initial insertion of needle/obturator assembly, allowing communication of passageway 116 with passageway 112.

Passageways 108, 116, 112 have smooth internal flow path radii in the flow path section. Generally, passageways 108, 116, and 112 (as well as control entry 126, needle/obturator assembly, and entrance lumens 22 of device 10) are of round form, preferably, but can be square or triangular or oval form or other shape.

When obturator is removed from hub after subcutaneous insertion of needle/obturator assembly into device 10, but prior to the start of the treatment session, sealed plug portion 130 self-seals the communication, thereby preventing fluid flow through passageway 116 during treatment. To further ensure that fluid is not lost through passageway 116 during treatment, a cap 132 can be secured to operating handle 114 at control entry 126 by means of lip 134, which may optionally take the form of a screw thread or other shape capable of cooperating with the internal shape of cap to ensure a secure fit of cap to operating handle 114.

Operating handle 114 is provided with locking means having a joining surface that forms alternating recesses 136 and protrusions 138 such that, when two hub structures are used with a device 10 having at least two passageways 22, the respective joining surfaces of the hub structures 110 may be matingly fitted together, as shown in FIG. 8A, to prevent rotational movement of either hub structure or their related needle cannulae when the cannulae are inserted into the device 10. Moving of either hub structure away from the other will allow rotational movement of either hub structure 110, as necessary for withdrawal of needle canulae. FIG. 8B show a wrapping 140 around the two structures will retain each to the other in a locking fashion.

Variants

There can be non-annular forms of the locking device. For example, the parts shown as annular pieces or arrays in FIGS. 2–3 can be part-annular. The locking blades can be of various other forms, e.g., blocks, balls, rollers. Springs or coil or leaf or other types can be used to assist locking or unlocking actions. The locking action can involve inscribing a cannula outer surface, holding it by friction or geometric blocking of a locking element with a rib or other protrusion on such surface. The plug seal and/or its closing bias spring can be of various forms and of different materials as are known in the art.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A subcutaneously implantable access device for access to a human or animal patient's vascular system for high fluid flow rate exchange of blood, consistent with hemodialysis, between the vascular system and an external processing apparatus, said access device comprising:

a first substantially straight through channel having an interior surface with a distal end and a proximate end with reference to the patient's skin, a guide constructed as movable between an open and a closed condition said guide located at the proximate end within the channel, said guide having a first and a second end, the first end with a hard rigid surface for accepting a tip of a percutaneous needle, wherein the accepting of said tip drives the guide to the open condition and aligns the needle with said channel, and removing the tip causes the guide to resume the closed condition, a seal positioned in said channel and having a through path aligned with said channel, the seal having an open state and a closed state, and the seal constructed in intimate contact with the second end of said guide, wherein when said needle assembly is aligned with said channel, the tip is aligned to penetrate said through path.

2. The access device of claim 1 wherein said guide comprises:

two opposing elements, and means for forcing said elements together, said means for forcing fixed relative to the opposing elements and to the access device.

3. The access device of claim 2 wherein said opposing elements are tapered, and where the means for forcing is a spring.

4. The access device of claim 1 further comprising:

a needle assembly comprising, an obturator positioned within the lumen of the needle assembly, said obturator forming the tip of the needle, that contacts and drives open said guide and said seal, and wherein said guide hard rigid surface is constructed with a hardness greater than the needle assembly and obturator hardness.

5. The access device of claim of claim 1 wherein said needle assembly comprises:

a cannula having a wall thickness of about 0.07 to about 0.15 mm and rigidity sufficient to maintain said guide in the open condition and said seal in the open state, and an obturator matingly inserted in said cannula, said obturator with a pointed end constructed for opening said guide and said seal.

6. The access device of claim 1 for transferring fluid into and/or out of a human or animal body further comprising:

a mount for said access device, means for attaching said mount to the surrounding tissue, means for movably attaching said access device to said mount wherein said device can move relative to the skin surface thereby providing virgin skin for piercing.

7. The access device of claim 1, wherein the intimate contact of the seal and the second end of the guide comprises means for joining the second end of the guide to said seal such that the guide in moving towards its open condition causes the through path of the seal to open thereby allowing the tip of the needle to penetrate into the through path without contacting the seal.

8. The access device of claim 7 wherein said seal is a solid resilient plug and where said through path is a slit through said plug.

9. The access device of claim 8 further comprising an elastomer wrapped around the plug providing a force that acts to close said slit.

10. The access system as defined in claim 1 wherein said proximate end of the interior surface of said substantially straight through channel comprises a generally sloped surface for receiving and directing said needle tip to the guide.

11. The access device of claim 1 further comprising a second substantially straight through channel having an interior surface and a distal end and a proximate end with reference to the patient's skin, and said proximate end arranged to receive one needle assembly tip, a second guide constructed as movable between an open and a closed condition said guide located at the proximate end within the channel, said second guide having a first and a second end, the first end with a hard rigid surface for accepting a tip of a percutaneous needle, wherein the accepting of said tip drives the second guide to assume the open condition and aligns the needle with said second channel, and removing the tip causes the second guide to resume the closed condition, a second seal positioned in said second channel and having a through path aligned with said second channel and an open state and a closed state, said second seal constructed in intimate contact with the second end of said second guide, wherein when the needle is aligned with said second channel, the tip is aligned to penetrate said through path.

12. In a subcutaneous access device for transfer of fluid into and/or out of a human or animal body and defining at least one internal passage within said access device, where each said internal passage provides access at one end proximate the skin for receiving a cannula passing through the skin, said cannula having an axis and defining an axial direction, and at the distal end by connecting to a catheter, the improvement therein comprising:

a blade resiliently attached within said access device, said blade set along the internal passage in the axial direction, and said blade having an edge, said edge defining, with respect to the skin, a distal portion and a proximate portion, wherein said edge is set at an angle with respect to the axis such that the distal portion of the edge intersects the internal passage wherein the distal portion of the edge contacts said cannula providing a radial force on said cannula, and wherein said resilient attachment of the blade within said device allows the blade to move in the radial and tangential directions with respect to the cannula, such that twisting the cannula drags the edge of the blade tangentially which reduces the radial force of the blade on the cannula and allows the cannula to be removed.

13. The device as defined in claim 12 wherein two or more blades are provided.

14. A hemodialysis access system for access to a human or animal patient's vascular system for high fluid flow rate exchange of blood between the vascular system and an external processing apparatus at a volumetric flow rate in excess of 250 ml/minute, and comprising, in combination, (a) a needle assembly comprising a lumen defined by an interior surface and constructed and arranged for puncturing the skin of the patient and for carrying blood therethrough at a flow rate consistent with high blood flow requirement of the blood exchange process;

(b) a subcutaneously implantable access device permitting fluid connection to a vessel or space within a patient's body, the device comprising:

(i) a substantially straight-through channel structure having an interior surface and a distal end and a proximal end with reference to the patient's skin puncture site and constructed and arranged for insertion of the needle through the proximal end of the channel and withdrawal of the needle therefrom, (ii) a seal arranged within the channel and movable between first and second positions, where said seal, in said first position, with said needle not inserted through said seal, prevents fluids from passing said seal and, in said second position, with said needle inserted through said seal, allows fluids to pass through said needle and emerge substantially at said channel distal end, and where blood flowpath transitions between said needle interior surface and said channel interior surface are substantially continuous and smooth when said means for sealing is in said second position; and the device further comprising structure for joining said channel distal end to a catheter that extends to an internal vessel of the body, and wherein such joining is continuous and smooth along said interior surfaces of the channel and catheter.

15. An access system as defined in claim 14 further comprising:

(c) a catheter constructed and arranged for implantation between said device at a proximal catheter end and to or into a patient blood vessel at a distal catheter end, and (d) means for attaching the catheter to the surrounding patient tissue, said attachment allowing movement of the catheter's proximal end and of said device.

16. A system as defined in claim 14 for high flow rate blood exchange between a human or animal patient with simultaneous flow in and out of the patient through separate paths, comprising a subcutaneously implantable access device capable of being implanted in the patient just under the skin and having two passages therein, each with an entrance proximal to the skin and an exit distal therefrom, for accommodating two hollow needles, with interior lumens, percutaneously inserted therein, the transitions between the interior lumens of the needles and passage interiors of the device forming substantially straight and streamlined flowpaths, thereby permitting fluid connection to one or two blood vessels within a patient's body.

17. A hemodialysis access system comprising:

(a) means for providing a continuous flowpath, crossing the patient's skin, between an external-to-patient dialysis site and an internal blood vessel of the patient, said means including a flow conduit whose internal surfaces are smooth and free of abrupt changes in flow area and direction and define a flowpath sized for hemodialysis flow rates, and free of obstructions to provide low flow resistance and avoid stagnation points;

(b) means for blocking the flowpath at a point under the patient's skin; and (c) means for removing the flowpath portion crossing the patient's skin; to allow closure and healing of the skin crossing site.

18. The system of claim 17 further comprising a flexible seal and wherein flowpath blockage is provided by said flexible seal, the flexible seal being entirely removable from the flowpath to establish a fully open configuration thereof free of obstructions and abrupt flow diameter or flow direction changes.

19. The system of either of claims 18 and further comprising means for locking and unlocking the flowpath forming portion of the system.

20. The system of either of claims 17 and further comprising means for increasing the available skin-crossing sites used in establishing the flowpath.

21. The system of claim 20 comprising a hollow needle which is insertable percutaneously by longitudinal pushing of it to a site where it defines a portion of said flowpath, and withdrawable by longitudinal pulling of said needle, and an implanted catheter comprising another portion of the flowpath and means for establishing a smooth continuous transition between said portions.

22. The system of claim 21 and further comprising means for locking the inserted needle in place and wherein said locking means are constructed and arranged to lock the needle upon longitudinal insertion movement and unlock and lock it upon longitudinal withdrawal movement accompanied by a lateral twisting movement.

23. The system of claim 22 and further comprising an obturator within the hollow needle and wherein said obturator has a pointed end arranged to protrude from a hollow needle end.

24. The system of claim 17 wherein said flow conduit comprises wall elements which have an angle relative to the flow direction such that blood cells are not damaged at hemodialysis flow rates.

* * * * *